(12) United States Patent
Bonvoisin et al.

(10) Patent No.: US 7,090,831 B1
(45) Date of Patent: Aug. 15, 2006

(54) PHARMACEUTICAL AEROSOL FORMULATION

(75) Inventors: Cecile Isabelle Bonvoisin, Evreux (FR); Christophe Laroche, Evreux (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/958,788

(22) PCT Filed: Apr. 13, 2000

(86) PCT No.: PCT/GB00/01418

§ 371 (c)(1),
(2), (4) Date: Oct. 15, 2001

(87) PCT Pub. No.: WO00/61108

PCT Pub. Date: Apr. 13, 2000

(30) Foreign Application Priority Data

Apr. 14, 1999 (BH) .......................... GCC/P/99/126
Sep. 10, 1999 (GB) ................................. 9921289.6

(51) Int. Cl.
*A61K 9/14* (2006.01)
*A61K 31/137* (2006.01)

(52) U.S. Cl. .................... 424/46; 424/489; 424/502; 514/716; 514/730

(58) Field of Classification Search ............. 424/400, 424/489, 502, 43, 45, 46; 514/730, 716
See application file for complete search history.

(56) References Cited

U.S. PATENT DOCUMENTS

| 4,992,474 | A |   | 2/1991  | Skidmore et al. |        |
|-----------|---|---|---------|-----------------|--------|
| 5,091,422 | A |   | 2/1992  | Skidmore et al. |        |
| 5,126,375 | A |   | 6/1992  | Skidmore et al. |        |
| 5,225,445 | A |   | 7/1993  | Skidmore et al. |        |
| 5,380,922 | A |   | 1/1995  | Beach et al.    |        |
| 5,849,265 | A | * | 12/1998 | Li-Bovet et al. | 424/45 |
| 6,153,173 | A | * | 11/2000 | Sapsford et al. | 424/45 |
| 6,482,438 | B1|   | 11/2002 | Singh et al.    |        |

FOREIGN PATENT DOCUMENTS

| EP | 0 257915    |   | 3/1988  |
|----|-------------|---|---------|
| EP | 0 550031    |   | 7/1993  |
| EP | 0655 237 A  |   | 5/1995  |
| EP | 0-556239    |   | 8/1995  |
| EP | 0-493437    |   | 8/1999  |
| GB | 1535531     | * | 12/1978 |
| WO | WO 91/16882 |   | 11/1991 |
| WO | WO 92/08446 |   | 5/1992  |
| WO | WO92 08447 A|   | 5/1992  |
| WO | WO 93/11743 |   | 6/1993  |
| WO | WO 93/11744 |   | 6/1993  |
| WO | WO 93/11745 |   | 6/1993  |
| WO | WO 94/03153 |   | 2/1994  |
| WO | WO97/35562  |   | 10/1997 |
| WO | WO 98/29096 |   | 7/1998  |
| WO | WO 98/29098 |   | 7/1998  |
| WO | WO99 53901 A|   | 10/1999 |

OTHER PUBLICATIONS

Seray-Pro, Apr. 1927.*
Barr Aerosol Dosage Forms pp. 675-678, Nov. 1958.*

* cited by examiner

*Primary Examiner*—Neil S. Levy
(74) *Attorney, Agent, or Firm*—J. Michael Strickland

(57) ABSTRACT

The present invention relates to novel pharmaceutical aerosol formulations comprising: (A) salmeterol xinafoate in the form of particles coated by spray-drying with at least one surfactant in the absence of any other coating excipient, in suspension in (B) a liquefied propellant gas which is 1,1,1,2,3,3,3-heptafluoro-n-propane or 1,1,1,2-tetrafluoroethane and mixtures thereof for administration particularly by the pulmonary route and to a process for preparing these formulations. It also relates to novel particles suitable for use in such formulations.

14 Claims, No Drawings

PHARMACEUTICAL AEROSOL FORMULATION

This application is filed pursuant to 35 U.S.C. §371 as a United States National Phase Application of International Application No. PCT/GB00/01418 filed 13 Apr. 2000 which claims priority from GCC/P/99/126 filed 14 Apr. 1999 in Bahrain and GB9921289.6 filed 10 Sep. 1999 in the United Kingdom.

The present invention relates to novel pharmaceutical aerosol formulations for the administration of salmeterol xinafoate particularly by the pulmonary route and to a process for preparing these formulations. It also relates to novel particles suitable for use in such formulations.

The use of aerosols for the administration of medicaments by the peripheral aerial pathways has been known for several decades. Such aerosols generally contain the therapeutic agent, one or more adjuvants such as solvents or surfactants and one or more propellants.

The most commonly used propellants in the past are chlorofluorocarbons, such as $CCl_3F$ (Freon® 11), $CCl_2F_2$ (Freon® 12) or $CF_2ClCF_2Cl$ (Freon® 114). However, the recent phasing out of these propellant gases due to their harmful effect on the ozone layer has caused manufacturers of aerosol sprays to use new propellant gases which protect stratospheric ozone.

Such "ozone-friendly" gases, also known as green gases, for example encompass hydrogen-containing chlorofluorocarbons, hydrogen-containing fluorocarbons and perfluorocarbons.

A specific group of therapeutic agents administered by the pulmonary route are antiasthmatics including bronchodilators and antiinflammatories of steroid type having a local therapeutic action in the lungs and/or a systemic therapeutic action after absorption in the blood. 4-hydroxy-$\alpha^1$-[[[6-(4-phenylbutoxy)hexyl] amino]methyl]-1,3-benzenedimethanol was described as one of a wide range of bronchodilators in GB-A-2140800. This compound is also known by the generic name of salmeterol, the xinafoate salt of which has become widely known as a highly effective treatment of inflammatory diseases, such as asthma and chronic obstructive pulmonary disease (COPD).

For medicaments such as salmeterol xinafoate, the replacement of the usual chlorofluorocarbon propellants by the novel propellants which protect the ozone layer can be accompanied by problems of stability of the suspensions. This is because the change in the polarity of the propellant sometimes results in a partial solubility of salmeterol xinafoate in the liquefied gas. This partial solubility may lead to an undesirable increase in the size of the particles during storage and/or the formation of aggregates. Formulations of salmeterol xinafoate in hydrofluoroalkane (HFA) propellant are known to be susceptible to absorption of the drug into the rubber components of the valves of the administration device. This may then cause the valves to seize resulting in a reduction of fine particle mass and/or the aggregates of particles will penetrate less well into the fine lower respiratory pathways, subsequently causing problems with dose uniformity.

International Patent Application No. WO 92/08446 (Glaxo Group Limited) discloses surfactant coated drug particles, however, such a formulation specifically requires a co-solvent. European Patent Application No. EP-A-0 493437 (Riker Laboratories Inc) discloses the presence of surfactants in a pharmaceutical aerosol formulation, however, the use of salmeterol xinafoate in such a formulation is not described. European Patent No. EP-A-0 556239 (Glaxo Group Limited) discloses surfactant coated medicaments, however, drying is performed by evaporation of the solvent and the use of 'spray-drying' is not described. WO 94/03153 (Glaxo Group Limited) discloses a suspension formulation of beclomethasone dipropionate, but specifically excludes the presence of a surfactant. WO 93/11743, WO 93/11744 and WO 93/11745 (Glaxo Group Limited) also disclose suspension formulations of drugs which specifically exclude the presence of surfactant. WO 97/35562 (Danbiosyst) describes a composition of spray dried medicaments, however, polysaccharides are incorporated and the use of surfactants in such a composition is not described. EP-A-257915 (Innovata) also describes a formulation comprising a spray-dried drug microcapsule, however, the use of salmeterol xinafoate in such a formulation is not described; furthermore, there is no disclosure of their use in formulations containing a liquefied propellant gas. WO 91/16882 (Liposome Technology) discloses a process for spray drying a drug/lipid-containing ethanol solution, but there is no mention of employing a surfactant in this process. EP-A-655237 (Hoechst) discloses pressurised aerosol formulations containing spray-dried product, wherein the spray-dried product is obtained by spray-drying a solution of drug, surfactant and (optionally) auxiliary substance to give a finely dispersed matrix, however, there is no mention of salmeterol xinafoate. International Patent Application Nos. WO 98/29096 and WO 98/29098 (Inhale Therapeutic Systems) describe the use of spray-drying a hydrophilic component and a hydrophobic component (eg. lactose), optionally stabilised by a surfactant, to provide dry powders with uniform characteristics.

We have now discovered that it is possible to improve the stability of suspensions of salmeterol xinafoate in the propellant by providing the drug particles with a spray-dried coating of surfactant in the absence of any other coating excipient. This protective layer apparently prevents the partial solubilization of the drug in the propellant and the formation of aggregates. It is thus possible to obtain aerosol formulations for pulmonary administration which, when protected from atmospheric moisture, are stable for months and make it possible to deliver drug particles having sizes which are sufficiently small to penetrate into the respiratory pathways.

A first subject of the present invention is consequently a pharmaceutical aerosol formulation comprising salmeterol xinafoate in the form of particles coated by spray-drying with surfactant in the absence of any other coating excipient in suspension in a liquefied propellant gas. A further subject of the present invention is the process for preparing these particles and pharmaceutical formulations. A still further subject are the spray-dried coated salmeterol xinafoate particles. Further subjects will become apparent to those skilled in the art from the following description and examples.

The present invention thus provides a pharmaceutical aerosol formulation comprising (A) salmeterol xinafoate in the form of particles coated by spray-drying with at least one surfactant in the absence of any other coating excipient, in suspension in (B) a liquefied propellant gas which is 1,1,1,2,3,3,3-heptafluoro-n-propane or 1,1,1,2-tetrafluoroethane and mixtures thereof.

According to the present invention, the salmeterol xinafoate particles are coated with at least one surfactant. This surfactant must be physiologically acceptable when it is used by inhalation, it must also be insoluble (or essentially insoluble) in the liquefied propellant gas or gases and must not have affinity therewith.

Examples of surfactants which can be used according to the present invention are anionic surfactants such as oleic acid, non-ionic surfactants such as sorbitan trioleate, sorbitan monooleate, sorbitan monolaurate, polyoxyethylene (20) sorbitan monolaurate, polyoxyethylene (20) sorbitan monooleate (Polysorbate 80), natural lecithin, oleyl polyoxyethylene (2) ether, stearyl polyoxyethylene (2) ether, lauryl polyoxyethylene (4) ether, block copolymers of ethylene oxide and of propylene oxide, synthetic lecithin, diethylene glycol dioleate, tetrahydrofurfuryl oleate, ethyl oleate, isopropyl myristate, glyceryl monooleate, glyceryl monostearate, glyceryl monoricinoleate, glyceryl ricinoleate 30 OE, glyceryl ricinoleate 60 OE, cetyl alcohol, stearyl alcohol, polyethylene glycol 400 or glyceryl monolaurate, or cationic surfactants, such as cetylpyridinium chloride or benzalkonium chloride. Other examples of surfactants include synthetic phosphatides eg. distearoylphosphatidylcholine.

Preferably a single surfactant will be used.

Use will preferably be made of lecithin, polyoxyethylene (20) sorbitan monooleate (Polysorbate 80), sorbitan monolaurate, glyceryl ricinoleate 30 OE and glyceryl ricinoleate 60 OE. Particularly preferred surfactants include lecithin and sorbitan monolaurate. Lecithin is most especially preferred; sorbitan monolaurate is also especially preferred.

As indicated above the particles of salmeterol xinafoate are coated by spray-drying with at least one surfactant in the absence of any other coating excipient. In particular the use of sugars as coating excipients is avoided.

The propellant is preferably 1,1,1,2,3,3,3-heptafluoro-n-propane (HFA227) or 1,1,1,2-tetrafluoroethane (HFA 134a), especially 1,1,2-tetrafluoroethane.

The coated salmeterol xinafoate particles of the aerosol formulations of the present invention must have sizes which allow them to be administered by inhalation. The particles must be sufficiently small, on the one hand, to penetrate into the pulmonary pathways without encountering obstacles and, on the other hand, they must have a sufficiently large size to deposit in the lung and not to be carried away by exhalation. The penetration of the salmeterol xinafoate particles as far as the pulmonary bronchioli and alveoli is generally only considered possible for particles having a mean size of less than 20 µm, preferably of less than 5 µm. The size of the spray-dried coated salmeterol xinafoate particles of the present invention is preferably within the range from 0.5 µm to 10 µm, in particular from 1 µm to 5 µm.

The pharmaceutical compositions according to the invention may also comprise other pharmaceutically acceptable ingredients such as co-solvents or surfactants. In a preferred embodiment of the present invention, the formulations contain no surfactant besides that coated on the salmeterol xinafoate particles and no co-solvents.

The pharmaceutical compositions according to the invention may also be used in combination with other therapeutic agents, for example anti-inflammatory agents (such as corticosteroids (eg. fluticasone propionate, beclomethasone dipropionate, mometasone furoate, triamcinolone acetonide, rofleponide or budesonide) or NSAIDs (eg. sodium cromoglycate, nedocromil sodium, PDE-4 inhibitors, leukotriene antagonists, iNOS inhibitors, tryptase and elastase inhibitors, beta-2 integrin antagonists and adenosine 2a agonists)) or other beta adrenergic agents (such as salbutamol, formoterol, fenoterol or terbutaline and salts thereof) or antiinfective agents (eg. antibiotics, antivirals).

According to the invention there is most preferred a pharmaceutical aerosol formulation which consists of
 (A) salmeterol xinafoate in the form of particles coated by spray-drying with at least one surfactant in the absence of any other coating excipient, in suspension in
 (B) a liquefied propellant gas which is 1,1,1,2,3,3,3-heptafluoro-n-propane or 1,1,1,2-tetrafluoroethane and mixtures thereof.

The present invention also provides a method for preparing a pharmaceutical aerosol formulation which comprises coating saimeterol xinafoate particles by spray-drying with at least one surfactant in the absence of any other coating excipient and in packaging them, together with the propellant, in a pressurised cartridge.

The process for the preparation of the pharmaceutical aerosol formulation of the present invention comprises, more specifically, the stages which consist
 (a) in preparing a suspension containing
  salmeterol xinafoate in the form of particles,
  a suspending medium which is a non-solvent for salmeterol xinafoate, and
  one or more surfactants dispersed in the suspending medium;
 (b) in spray drying the suspension obtained in stage (a), so as to obtain salmeterol xinafoate particles coated by spray-drying with the surfactant(s);
 (c) in suspending the coated salmeterol xinafoate particles obtained in stage (b) in the liquefied propellant gas.

The particles of salmeterol xinafoate used in step (a) will also be of size suitable for inhalation eg. of mean size less than 20 µm (eg. 0.5 µm–10 µm) preferably less than 5 µm (eg. 1 µm–5 µm).

In one embodiment of the process of the invention, the suspension of stage (a) above is prepared by dispersing the surfactant(s) in the said suspending medium and by subsequently dispersing the salmeterol xinafoate particles in the suspension thus obtained.

It is also possible, according to another embodiment of the process of the invention, to adsorb, in a first step, the surfactant on the uncoated salmeterol xinafoate particles and subsequently to disperse the particle/surfactant combination in the suspending medium.

The suspending medium used for coating of the salmeterol xinafoate particles has to be essentially non solvent for the therapeutic agent (eg. where the solubility of salmeterol xinafoate in the suspending medium is less than around 0.1 mg/ml). The preferred suspending medium is water. The content of salmeterol xinafoate in the suspension prepared in stage (a) can vary within wide limits. It is generally within the range from 1 to 40% (mass/volume), preferably in the range from 1 to 20%, eg. 5% (mass/volume).

The content of surfactant in the suspension prepared in stage (a) is generally between 0.001 and 5% by weight, preferably between 0.001 and 1% by weight.

When the content of salmeterol xinafoate in the suspension prepared in stage (a) is around 5% (mass/volume) the content of surfactant in the dried product prepared in stage (b) is generally between 0.01 and 20% by weight, preferably between 0.05 and 10% by weight.

The suspension described above is subsequently subjected to spray drying in an appropriate device. The suspension to be dried is dispersed as fine droplets in a stream of hot air, which instantaneously transforms them into small grains of powder. A person skilled in the art would know how to adjust the operating parameters, such as the flow rate of the suspension arriving in the drying chamber, the size of the nozzle, the inlet and outlet temperature, the atomising pressure and the flow rate of the atomising air, according to the recommendations of the manufacturer and as a function of the characteristics of the product which he desires to obtain.

A suitable spray dryer which makes possible the drying of the salmeterol xinafoate particles of the present invention is the Büchi 191 Mini Spray Dryer (Büchi Company, Switzerland). Typical physical parameters of the atomisation in such a device which make it possible to obtain the coated particles of active principle from the suspension of stage (a) are as follows:

Inlet air temperature: 105° C.
Outlet air temperature: 50–70° C.
Compressed air pressure: 7 bar
Atomising air flow rate: 800 NL/h
Drying air flow: 28 m$^3$/h
Feed flow: 4–5 ml/min wherein NL represents 'normal liter' i.e a liter of gas administered at normal temperature (25° C.) and normal pressure (1 atmosphere).

The spray-dried material obtained is generally composed of particles having a mean size of between 1 μm and 10 μm and a water content of between 0.01 and 0.5% by weight.

If necessary, the particles obtained by spray drying can be subjected to size reduction eg. micronisation or to any other method which is able to reduce their mean size to a value of less than 10 μm and preferably of less than 5 μm, before suspension in the propellant. Indeed, spray drying may result in partial aggregation of the particles bound to each other by the coating layer, this aggregation increasing substantially the apparent mean size of the particles. The main purpose of this step is to break up these aggregates. It is optional and its usefulness depends, of course, on the presence of aggregates, in other words on the size of the particles after spray drying.

Micronisation is carried out in devices known as compressed-air micronisers or fluid jet mills. In these devices, the particles are carried by a strong stream of air into a chamber designed so that the particles are subjected therein to a large number of impacts. In order to obtain coated salmeterol xinafoate particles having an appropriate size, these devices will be made to operate at a pressure of between 6 and 14 bar, preferably between 8 and 12 bar.

The cartridges may be filled by any means which makes it possible to obtain a homogeneous suspension of the coated salmeterol xinafoate particles in the propellant. The cartridges can be filled, for example, first with the particles and then with the propellant ('dual stage') or alternatively with a prepared suspension of the particles in the propellant ('single stage').

This filling will preferably be carried out in a controlled atmosphere with a low relative humidity, in order to limit the hydration of the particles during filling.

Cartridges will generally be fitted with a metering valve and a metered dose inhaler (MDI) will comprise such a cartridge and valve together with a channelling device suitable for delivery of the formulation to the lung.

The cartridges are preferably but not necessarily stored in a packaging composed of a film which is impermeable to atmospheric moisture. The suspensions contained in these overwrapped cartridges are expected to be stable for several months at room temperature (25° C.). Other means to resist ingress of moisture to the canister may also be employed.

As a further aspect of the invention we present a process for the preparation of a pharmaceutical aerosol formulation according to the present invention characterised in that it comprises overwrapping filled cartridges with a film which is impermeable to atmospheric moisture.

A further aspect of the invention is salmeterol xinafoate in the form of particles coated by spray-drying with at least one surfactant in the absence of any other coating excipient suitable for use, in combination with a propellant gas, in a pharmaceutical aerosol formulation according to the present invention.

As a further aspect of the invention we present salmeterol xinafoate in the form of particles coated by spray-drying with at least one surfactant in the absence of any other coating excipient obtainable by a process which comprises the stages which consist
(a) in preparing a suspension containing
    salmeterol xinafoate in the form of particles,
    a suspending medium which is a non-solvent for salmeterol xinafoate, and
    one or more surfactants dispersed in the suspending medium;
(b) in spray drying the suspension of the active principle obtained in stage (a), so as to obtain salmeterol xinafoate particles coated by the surfactant(s).

Cartridges containing a formulation according to the present invention also form an aspect of the invention.

EXAMPLES

The following examples are intended to illustrate the invention but do not have a limiting nature.

Example 1

0.2 g of lecithin may be dissolved in 200 ml of demineralized water at room temperature (20° C.±2° C.). 10 g of salmeterol xinafoate as micronised particles may be dispersed under stirring in the lecithin aqueous solution. The suspension thus obtained contains 5% salmeterol xinafoate and 0.1% lecithin. This suspension may then be spray-dried in a Büchi 191 Mini Spray Dryer with the following parameters:

Inlet air temperature: 105° C.
Outlet air temperature: 58° C.
Compressed air pressure: 7 bars
Atomising air flow rate: 800 NL/h
Drying air flow: 28 m$^3$/h
Feed flow: 5 ml/min The yield of the spray drying is around 70% (eg. 73%).
The water content of powder is less than 0.5% (w/w). The particles before being micronised have a mean diameter between 2 and 5 μm.

The spray dried material obtained may be micronised in a fluid jet mill (MC 50, JET Pharma S.A.) under a pressure of 8 bars.

The characteristics of the particles before being placed in canisters are as follows:
mean diameter around 1.5 μm water content: 0.03% (w/w)

The canisters are filled manually in a controlled atmosphere room (20±2° C., relative humidity of less than 15%) by successively introducing the micronised material and then pressurised HFA134a gas.

Example 2

1 g of lecithin may be dissolved in 200 ml of demineralized water at room temperature (20° C.±2° C.). 10 g of salmeterol xinafoate as micronised particles may be dispersed under stirring in the lecithin aqueous solution. The suspension thus obtained contains 5% salmeterol xinafoate and 0.5% lecithin.

This suspension may then be spray-dried in a Büchi 191 Mini Spray Dryer operating with the following parameters:
Inlet air temperature: 105° C.
Outlet air temperature: 61° C.
Compressed air pressure: 7 bars
Atomising air flow rate: 800 NL/h
Drying air flow: 28 m$^3$/h
Feed flow: 5 ml/min
The yield of the spray drying is 65%.

The water content of powder is less than 0.5% (w/w). The particles before being micronised have a mean diameter between 2 and 5 µm.

The spray dried material obtained is micronised in a fluid jet mill (MC 50, JET Pharma S.A.) under a pressure of 8 bars.

The particles before being placed in canisters have a mean diameter around 1.5 µm.

The canisters are filled manually in a controlled atmosphere room (20±2° C., relative humidity of less than 15%) by successively introducing the micronised material and then pressurised HFA134a gas.

Example 3

0.2 g of Montane 20 (sorbitan monolaurate) may be dissolved in 200 ml of demineralized water at room temperature (20° C.±2° C.). 10 g of salmeterol xinafoate as micronised particles may be dispersed under stirring in the Montane 20-aqueous solution. The suspension thus obtained contains 5% salmeterol xinafoate and 0.1% Montane 20.

This suspension may then be spray-dried in a Büchi 191 Mini Spray Dryer operating with the following parameters:
Inlet air-temperature: 105° C.
Outlet air temperature: 50° C.
Compressed air pressure: 7 bar
Atomising air flow rate: 800 NL/h
Drying air flow: 28 m$^3$/h
Feed flow: 5 ml/min
The yield of the spray drying is 69%.

The water content of powder is less than 0.5% (w/w). The particles before being micronised have a mean diameter between 2 and 5 µm.

The spray dried material obtained is micronised in a fluid jet mill (MC 50, JET Pharma S.A.) under a pressure of 8 bars.

The characteristics of the particles before being placed in canisters are as follows:
mean diameter around 1.5 µm
water content: 0.02%

The canisters are filled manually in a controlled atmosphere room (20±2° C., relative humidity of less than 15%) by successively introducing the micronised material and then pressurised HFA134a gas.

Example 4

0.2 g of Montanox 80 (Polysorbate 80) may be dissolved in 200 ml of demineralized water at room temperature (20° C.±2° C.). 10 g of salmeterol xinafoate as micronised particles may be dispersed under stirring in the Montanox 80 aqueous solution. The suspension thus obtained contains 5% salmeterol xinafoate and 0.1% Montanox 80.

This suspension is then spray-dried in a Büchi 191 Mini Spray Dryer operating with the following parameters:
Inlet air temperature: 105° C.
Outlet air temperature: 50° C.
Compressed air pressure: 7 bar
Atomising air flow rate: 800 NL/h
Drying air flow: 28 m$^3$/h
Feed flow: 5 ml/min
The yield of the spray drying is 75%.

The water content of powder is less than 0.5% (w/w). The particles before being micronised have a mean diameter between 2 and 5 µm.

The spray dried material obtained is micronised in a fluid jet mill (MC 50, JET Pharma S.A.) under a pressure of 8 bars.

The particles before being placed in canisters have a mean diameter around 1.5 µm.

The canisters are filled manually in a controlled atmosphere room (20±2° C., relative humidity of less than 15%) by successively introducing the micronised material and then pressurised HFA134a gas.

Example 5

0.2 g of Simulsol 5817 (glyceryl ricinoleate 30 OE) may be dissolved in 200 ml of demineralized water at room temperature (20° C.±2° C.). 10 g of salmeterol xinafoate as micronised particles may be dispersed under stirring in the Simulsol 5817 aqueous solution. The suspension thus obtained contains 5% salmeterol xinafoate and 0.1% Simulsol 5817.

This suspension may then be spray-dried in a Büchi 191 Mini Spray Dryer operating with the following parameters:
Inlet air temperature: 105° C.
Outlet air temperature: 59° C.
Compressed air pressure: 7 bar
Atomising air flow rate: 800 NL/h
Drying air flow: 28 m$^3$/h
Feed flow: 5 ml/min
The yield of the spray drying is 78%.

The water content of powder is less than 0.5% (w/w). The particles before being micronised have a mean diameter between 2 and 5 µm.

The spray dried material obtained is micronised in a fluid jet mill (MC 50, JET Pharma S.A.) under a pressure of 8 bars.

The particles before being placed in canisters have a mean diameter around 1.5 µm.

The canisters are filled manually in a controlled atmosphere room (20±2° C., relative humidity of less than 15%) by successively introducing the micronised material and then pressurised HFA134a gas.

Example 6

0.2 g of Simulsol 1285 DF (glyceryl ricinoleate 60 OE) may be dissolved in 200 ml of demineralized water at room temperature (20° C.±2° C.). 10 g of salmeterol xinafoate as micronised particles may be dispersed under stirring in the Simulsol 1285 DF aqueous solution. The suspension thus obtained contains 5% salmeterol xinafoate and 0.1% Simulsol 1285 DF.

This suspension may then be spray-dried in a Büchi 191 Mini Spray Dryer operating with the following parameters:
Inlet air temperature: 105° C.
Outlet air temperature 58° C.
Compressed air pressure: 7 bar Atomising air flow rate: 800 NL/h
Drying air flow: 28 m³/h
Feed flow: 5 ml/min
The yield of the spray drying is 54%.

The water content of powder is less than 0.5% (w/w). The particles before being micronised have a mean diameter between 2 and 5 μm.

The spray dried material obtained is micronised in a fluid jet mill (MC 50, JET Pharma S.A.) under a pressure of 8 bars.

The particles before being placed in canisters have a mean diameter around 1.5 µm.

The canisters are filled manually in a controlled atmosphere room (20±2° C., relative humidity of less than 15%) by successively introducing the micronised material and then pressurised HFA134a gas.

Example 7

1 g of Montane 20 (sorbitan monolaurate) may be dissolved in 200 ml of demineralized water at room temperature (20° C.±2° C.). 10 g of salmeterol xinafoate as micronised particles may be dispersed under stirring in the Montane 20 aqueous solution. The suspension thus obtained contains 5% salmeterol xinafoate and 0.5% Montane 20.

This suspension may then be spray-dried in a Büchi 191 Mini Spray Dryer operating with the following parameters:

Inlet air temperature: 105° C.

Outlet air temperature: 53° C.

Compressed air pressure: 7 bar

Atomising air flow rate: 800 NL/h

Drying air flow: 28 $m^3$/h

Feed flow: 5 ml/min

The yield of the spray drying is 73%.

The water content of powder is less than 0.5% (w/w). The particles before being micronised have a mean diameter between 2 and 5 µm.

The spray dried material obtained is micronised in a fluid jet mill (MC 50, JET Pharma S.A.) under a pressure of 8 bars.

The particles before being placed in canisters have a mean diameter around 1.5 µm.

The canisters are filled manually in a controlled atmosphere room (20±2° C., relative humidity of less than 15%) by successively introducing the micronised material and then pressurised HFA134a gas.

Example 8

0.5 g of Montane 20 (sorbitan monolaurate) may be dissolved in 99.5 ml of demineralized water at room temperature (20° C.±2° C.). Then 5 g of this solution are dissolved in 995 ml of demineralized water at room temperature. 20 g of salmeterol xinafoate as micronised particles are then dispersed under stirring in 400 ml of this Montane 20 aqueous solution. The suspension thus obtained contains 5% salmeterol xinafoate and 0.0025% Montane 20.

This suspension may then be spray-dried in a Büchi 191 Mini Spray Dryer operating with the following parameters:

Inlet air temperature: 105° C.

Outlet air temperature: 60° C.

Compressed air pressure: 7 bar

Atomising air flow rate: 800 NL/h

Drying air flow: 28 $m^3$/h

Feed flow: around 4 ml/min

The yield of the spray drying is around 60%.*

The water content of powder is 0.02% (w/w). The particles before being micronised have a mean diameter of 2.4 µm.

The spray dried material obtained is micronised in a fluid jet mill (MC 50, JET Pharma S.A.) under a pressure of 8 bars.

The characteristics of the particles before being placed in canisters are as follows:

mean diameter around 1.5 µm water content: 0.02%

The canisters are filled manually in a controlled atmosphere room (20±2° C., relative humidity of less than 15%) by successively introducing the micronised material and then pressurised HFA134a gas.

Example 9

0.5 g of Montane 20 (sorbitan monolaurate) may be dissolved in 99.5 ml of demineralized water at room temperature (20° C.±2° C.). Then 10 g of this solution are dissolved in 990 ml of demineralized water at room temperature. 20 g of salmeterol xinafoate as micronised particles are then dispersed under stirring in 400 ml of this Montane 20 aqueous solution. The suspension thus obtained contains 5% salmeterol xinafoate and 0.005% Montane 20.

This suspension may then be spray-dried in a Büchi 191 Mini Spray Dryer operating with the following parameters:

Inlet air temperature: 105° C.

Outlet air temperature: 60° C.

Compressed air pressure: 7 bar

Atomising air flow rate: 800 NL/h

Drying air flow: 28 $m^3$/h

Feed flow: around 4 ml/min

The yield of the spray drying is between 68 and 76%.

The water content of powder is 0.01% (w/w). The particles before being micronised have a mean diameter of 2.3 µm.

The spray dried material obtained is micronised in a fluid jet mill (MC 50, JET Pharma S.A.) under a pressure of 8 bars.

The characteristics of the particles before being placed in canisters are as follows:

mean diameter around 1.3 µm water content: 0.02%

The canisters are filled manually in a controlled atmosphere room (20±2° C., relative humidity of less than 15%) by successively introducing the micronised material and then pressurised HFA134a gas.

Example 10

5 g of Montane 20 (sorbitan monolaurate) may be dissolved in 95 ml of demineralized water at room temperature (20° C.±2° C.). Then 5 g of this solution are dissolved in 995 ml of demineralized water at room temperature. 20 g of salmeterol xinafoate as micronised particles are then dispersed under stirring in 400 ml of this Montane 20 aqueous solution. The suspension thus obtained contains 5% salmeterol xinafoate and 0.025% Montane 20.

This suspension may then be spray-dried in a Büchi 191 Mini Spray Dryer operating with the following parameters:

Inlet air temperature: 105° C.

Outlet air temperature: 63° C.

Compressed air pressure 7 bar

Atomising air flow rate: 800 NL/h

Drying air flow: 28 $m^3$/h

Feed flow: around 4 ml/min

The yield of the spray drying is around 77%.

The water content of powder is 0.02% (w/w). The particles before being micronised have a mean diameter of 2.4 µm.

The spray dried material obtained is micronised in a fluid jet mill (MC 50, JET Pharma S.A.) under a pressure of 8 bars.

The characteristics of the particles before being placed in canisters are as follows:

mean diameter around 1.5 µm water content: 0.02%

The canisters are filled manually in a controlled atmosphere room (20±2° C., relative humidity of less than 15%) by successively introducing the micronised material and then pressurised HFA134a gas.

Example 11

0.5 g of lecithin was dissolved in 99.5 ml of demineralized water at room temperature. 5 g of this solution was then dissolved in. 995 ml of demineralized water at room temperature. 20 g of salmeterol xinafoate as micronized particles were then dispersed under stirring in 400 ml of this lecithin aqueous solution. The suspension thus obtained contained 5% salmeterol xinafoate and 0.0025% lecithin.

This suspension was then spray-dried in a Büchi 191 Mini Spray Dryer operating with the following parameters:

Inlet air temperature: 105° C.

Outlet air temperature: 61° C.

Compressed air pressure: 7 bar

Atomising air flow rate: 800 NL/h

Drying air flow: 28 $m^3/h$

Feed flow: around 4 ml/min

The yield of the spray drying was around 70%.

The water content of powder was 0.01% (w/w). The particles before being micronized had a mean diameter between 2 and 5 µm.

The spray dried material obtained was micronized in a fluid jet mill (MC 50, company Jet Pharma) under a pressure of 8 bars.

The characteristics of the particles before being placed in canisters were as follows:

mean diameter around 1.5 µm water content: 0.01%

The canisters were filled manually in a controlled atmosphere room (20±2° C., relative humidity of less than 15%) by successively introducing the micronized material and then pressurised HFA134a gas.

Example 12

5 g of lecithin was dissolved in 95 ml of demineralized water at room temperature. 5 g of this solution was then dissolved in 995 ml of demineralized water at room temperature. 20 g of salmeterol xinafoate as micronized particles were then dispersed under stirring in 400 ml of this lecithin aqueous solution. The suspension thus obtained contained 5% salmeterol xinafoate and 0.025% lecithin.

This suspension was then spray-dried in a Büchi 191 Mini Spray Dryer operating with the following parameters:

Inlet air temperature: 105° C.

Outlet air temperature: 60° C.

Compressed air pressure: 7 bar

Atomising air flow rate: 800 NL/h

Drying air flow: 28 $m^3/h$

Feed flow: around 4 ml/min

The yield of the spray drying was around 75%.

The water content of powder was 0.01% (w/w). The particles before being micronized had a mean diameter between 2 and 5 µm.

The spray dried material obtained was micronized in a fluid jet mill (MC 50, company Jet Pharma) under a pressure of 8 bars.

The characteristics of the particles before being placed in canisters were as follows:

mean diameter around 1.5 µm water content: 0.01%

The canisters were filled manually in a controlled atmosphere room (20±2° C., relative humidity of less than 15%) by successively introducing the micronized material and then pressurised HFA134a gas.

Example 13

5 g of lecithin was dissolved in 95 ml of demineralized water at room temperature. 10 g of this solution was then dissolved in 990 ml of demineralized water at room temperature. 20 g of salmeterol xinafoate as micronized particles were then dispersed under stirring in 400 ml of this lecithin solution. The suspension thus obtained contained 5% salmeterol xinafoate and 0.05% lecithin.

This suspension, was then spray-dried in a Büchi 191 Mini Spray Dryer operating with the following parameters:

Inlet air temperature: 105° C.

Outlet air temperature: 60° C.

Compressed air pressure: 7 bar

Atomising air flow rate: 800 NL/h

Drying air flow: 28 $m^3/h$

Feed flow: around 4 ml/min

The yield of the spray drying was around 75%.

The water content of powder was 0.01% (w/w). The particles before being micronized had a mean diameter between 2 and 5 µm.

The spray dried material obtained was micronized in a fluid jet mill (MC 50, company Jet Pharma) under a pressure of 8 bars.

The characteristics of the particles before being placed in canisters were as follows:

mean diameter around 1.5 µm water content: 0.01%

The canisters were filled manually in a controlled atmosphere room (20±2° C., relative humidity of less than 15%) by successively introducing the micronized material and then pressurised HFA134a gas.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A process for the preparation of a pharmaceutical aerosol formulation that comprises:

(A) salmeterol xinafoate in the form of particles having a coating that comprises at least one surfactant, which surfactant is physiologically acceptable when used by inhalation, in the absence of any coating excipient that is a sugar, wherein the particles have a water content of between 0.01 and 0.5% by weight of the particles, in suspension in (B) a liquefied propellant gas which is 1,1,1,2,3,3,3-beptafluoro-n-propane or 1,1,1,2-tetrafluoroethane or mixtures thereof, wherein the at least one surfactant is essentially insoluble in the liquefied propellant gas and does not have an affinity therewith;

said process comprising:

providing a suspension comprising salmeterol xinafoate in the form of particles, a suspending medium that is water, and one or more surfactants;

spray drying the suspension producing salmeterol xinafoate particles coated with one or more surfactants; and, suspending the coated salmeterol xinafoate particles in liquefied propellant.

2. A process for the preparation of a pharmaceutical aerosol formulation according to claim 1, further comprising reducing the size of the coated particles obtained by spray drying before suspension in the propellant.

3. A process for the preparation of a pharmaceutical aerosol formulation according to claim 1, wherein the mean size of the coated drug particles is within the range from 0.5 to 10 μm.

4. A process for the preparation of a pharmaceutical aerosol formulation according to claim 3, wherein the mean size of the coated drug particles is within the range from 1 to 5 μm.

5. A process for the preparation of a pharmaceutical aerosol formulation according to claim 1, wherein the providing of the suspension comprises:

suspending salmeterol xinafoate in the form of particles in the suspending medium for salmeterol xinafoate; and dispersing one or more surfactants in the suspending medium.

6. A process for the preparation of a pharmaceutical aerosol formulation according to claim 1, wherein the providing of the suspension comprises:

dispensing one or more surfactants in the suspending medium to produce a colloidal solution; and subsequently dispersing the salmeterol xinafoate particles in the colloidal solution.

7. A process for the preparation of a pharmaceutical aerosol formulation according to claim 1, wherein the content of salmeterol xinafoate in the suspension is within the range from 1 to 40% (mass/volume).

8. A process for the preparation of a pharmaceutical aerosol formulation according to claim 7, wherein the content of salmeterol xinafoate in the suspension is in the range from 1 to 20% (mass/volume).

9. A process for the preparation of a pharmaceutical aerosol formulation according to claim 1, wherein the content of surfactant in the suspension is between 0.001 and 5% by weight.

10. A process for the preparation of a pharmaceutical aerosol formulation according to claim 9, wherein the content of surfactant in the suspension is between 0.001 and 1% by weight.

11. A process for the preparation of a pharmaceutical aerosol formulation according to claim 1, wherein the suspending of the coated salmeterol xinafoate particles in liquefied propellant comprises successively filling cartridges with the spray-dried particles and then filling the cartridges with the propellant.

12. A process for the preparation of a pharmaceutical aerosol formulation according to claim 1, further comprising filling cartridges with the coated salmeterol xinafoate particles suspended in liquefied propellant.

13. A process for the preparation of a pharmaceutical aerosol formulation according to claim 11, further comprising overwrapping filled cartridges with a film impermeable to atmospheric moisture.

14. A process for the preparation of a composition that comprises salmeterol xinafoate in the form of particles having a coating comprising at least one surfactant, which surfactant is physiologically acceptable when used by inhalation, in the absence of any coating excipient that is a sugar, wherein the particles have a water content of between 0.01 and 0.5% by weight of the particles, said process comprising:

preparing a suspension containing salmeterol xinafoate in the form of particles, a suspending medium which is waters and one or more surfactants dispersed in the suspending medium; and spray drying the suspension so as to obtain salmeterol xinafoate particles coated by the surfactant(s).

* * * * *